(12) United States Patent
DeBoer et al.

(10) Patent No.: US 8,771,347 B2
(45) Date of Patent: *Jul. 8, 2014

(54) ACCOMMODATING INTRAOCULAR LENS

(75) Inventors: Charles DeBoer, Pasadena, CA (US); Yu-Chong Tai, Pasadena, CA (US); Mark Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/350,612

(22) Filed: Jan. 13, 2012

(65) Prior Publication Data

US 2012/0303118 A1 Nov. 29, 2012

Related U.S. Application Data

(60) Provisional application No. 61/488,964, filed on May 23, 2011, provisional application No. 61/526,147, filed on Aug. 22, 2011.

(51) Int. Cl.
*A61F 2/16* (2006.01)

(52) U.S. Cl.
CPC ....... *A61F 2/1635* (2013.01); *A61F 2250/0003* (2013.01)
USPC ....... 623/6.13; 623/6.18; 623/6.37; 623/6.39; 623/6.59

(58) Field of Classification Search
USPC .............. 623/6.13, 6.18, 6.37, 6.39, 6.59, 6.6
See application file for complete search history.

(56) References Cited

U.S. PATENT DOCUMENTS

| 4,666,445 A | 5/1987 | Tillay |
| 4,822,360 A | 4/1989 | Deacon |
| 4,888,016 A | 12/1989 | Langerman |
| 4,995,880 A | 2/1991 | Galib |
| 5,035,710 A | 7/1991 | Nakada et al. |
| 5,091,121 A | 2/1992 | Nakada et al. |
| 5,213,579 A * | 5/1993 | Yamada et al. .............. 623/6.13 |

(Continued)

FOREIGN PATENT DOCUMENTS

| JP | 04132547 A | * | 5/1992 |
| WO | WO 2009021327 A1 | * | 2/2009 |

OTHER PUBLICATIONS

International Search Report and Written Opinion, Jul. 30, 2012, PCT application No. PCT/US2012/021366, 18 pages.

(Continued)

*Primary Examiner* — David H Willse
*Assistant Examiner* — Javier Blanco
(74) *Attorney, Agent, or Firm* — Kilpatrick Townsend & Stockton LLP

(57) ABSTRACT

Systems, devices, and methods are presented for a prosthetic injectable intraocular lens. One or more silicone elastomeric patches located outside the optical path on the anterior side but away from the equator can be accessed by surgical needles in order to fill or adjust optically clear fluid within the lens. The fluid can be adjusted in order to set a base dioptric power of the lens and otherwise adjust a lens after its initial insertion. The elastomeric patches are sized so that they self-seal after a needle is withdrawn. A straight or stepped slit in the patch can allow a blunt needle to more easily access the interior of the lens.

17 Claims, 13 Drawing Sheets

(56) References Cited

U.S. PATENT DOCUMENTS

| | | | |
|---|---|---|---|
| 6,358,279 | B1 | 3/2002 | Tahi et al. |
| 7,137,994 | B2 | 11/2006 | de Juan, Jr. et al. |
| 7,326,649 | B2 | 2/2008 | Rodger et al. |
| 7,569,048 | B2 * | 8/2009 | Brown ............ 604/541 |
| 7,774,931 | B2 | 8/2010 | Tai et al. |
| 7,806,929 | B2 * | 10/2010 | Brown ............ 623/6.39 |
| 7,883,540 | B2 * | 2/2011 | Niwa et al. ............ 623/6.13 |
| 2004/0068317 | A1 * | 4/2004 | Knight ............ 623/6.48 |
| 2005/0177169 | A1 * | 8/2005 | Fisher et al. ............ 606/88 |
| 2006/0047339 | A1 * | 3/2006 | Brown ............ 623/6.13 |
| 2006/0084949 | A1 | 4/2006 | Peyman |
| 2006/0178741 | A1 | 8/2006 | Zadno-Azizi et al. |
| 2007/0016294 | A1 * | 1/2007 | Greenberg et al. ............ 623/6.63 |
| 2007/0213818 | A1 * | 9/2007 | Carriazo ............ 623/6.13 |
| 2012/0310343 | A1 | 12/2012 | Van Noy |
| 2013/0053954 | A1 | 2/2013 | Rao et al. |

OTHER PUBLICATIONS

Chong, L.P., "A self-stabilizing lens ring for 25-gauge vitrectomy surgery," Am J Ophthalmol, vol. 143, No. 2, pp. 350-351, 2007.

Menapace, R. et al., "Accommodating intraocular lenses: a critical review of present and future concepts," Graefes Arch Clin Exp Ophthalmol, vol. 245, No. 4, pp. 473-489, 2007.

Alfonso, J.F. et al., "Prospective visual evaluation of apodized diffractive intraocular lenses," J Cataract Refract Surg, vol. 33, pp. 1235-1243, 2007.

Hermans, E. et al., "Development of a ciliary muscle-driven accommodating intraocular lens," J Cataract Refract Surg, vol. 34, pp. 2133-2138, 2008.

Ben-Nun, J. et al., "Feasibility and development of a high-power real accommodating intraocular lens," J Cataract Refract Surg, vol. 31, No. 9, pp. 1802-1808, 2005.

Wolffsohn, J. el al., "Subjective and objective performance of the Lenstec KH-3500"accommodative"intraocular lens," Br J Ophthalmol, vol. 90, pp. 693-696, 2006.

Zhao, G. et al., "Visual function after monocular implantation of apodized diffractive multifocal or single-piece monofocal intraocular lens: randomized prospective comparison," J Cataract Refract Surg, vol. 36, No. 9, pp. 282-285, 2010.

Cillino, S. et al., "One-year outcomes with new-generation multifocal intraocular lenses," Ophthalmology, vol. 155, pp. 1508-1516, 2008.

Glasser, A., "Restoration of accommodation: surgical options for correction of presbyopia," Clin Exp Optom, vol. 91, pp. 279-295, 2008.

Duane, A., "Normal values of the accommodation at all ages," JAMA, vol. 59, No. 12, pp. 1020-1013, 1912.

Koertz, J. et al., "Accommodation and presbyopia in the human eye—aging of the anterior segment," Vision Research, vol. 29, pp. 1685-1692, 1989.

David Atchison, G.S. *Optics of the Human Eye.* Oxford: Butterworth Heinemann. 2000, p. 18.

von Helmholtz, H. *Helmholtz's Treatise on Physiological Optics.* Optical Society of America, pp. 143-172, 1924.

Dubbelman, M. et al., "Change in shape of the aging human crystalline lens with accommodation," Vision Res, vol. 45, pp. 117-132, 2005.

Rosales, P. et al., "Crystalline lens radii of curvature from Purkinje and Scheimpflug imaging," J Vis, vol. 6, pp. 1057-1067, 2006.

Pau, H., et al., "The increasing sclerosis of the human lens with age and its relevance to accommodation and presbyopia," Graefes Arch Clin Exp Ophthalmol, vol. 226, No. 3, pp. 294-296, 1990.

Heys, K. et al., "Massive increase in the stiffness of the human lens nucleus with age: the basis for presbyopia?" Mol Vis, vol. 10, pp. 956-963, 2004.

Weeber, H.A. et al., "Sstiffness gradient in the crystalline lens," Graefes Arch Clin Exp Ophthalmol, vol. 245, pp. 1357-1366, 2007.

Glasser, a. et al., "Presbyopia and the optical changes in the human crystalline lens with age," Vision Research, vol. 38, No. 2, pp. 209-229, 1998.

Strenk, L. et al., "The mechanism of presbyopia," Progress in Retinal and Eye Research, vol. 24, No. 3, pp. 379-393, 2005.

Strenk, L. et al., "Age-related changes in human ciliary muscle and lens," Invest Ophthalmol Vis Sci, vol. 40, No. 6, pp. 1162-1169, 1999.

Cumming, J. et al., "Clinical evaluation of the Crystalens AT-45 accommodating intraocular lens: results of the U.S. Food and Drug Administration clinical trial," J Cataract Refract Surg, vol. 32. pp. 812-822, 2006.

Kasthurirangan, S. et al., "MRI study of the changes in crystalline lens shape with accommodation and aging in humans," J Vis, vol. 11, 2011.

Findl, O. at al., "Meta-analysis of accommodating intraocular lenses," J Cataract Refract Surg, vol. 33, pp. 522-527, 2007.

Ossma, I. et al., "Synchrony dual-optic accommodating intraocular lenses. Part 2: Pilot clinical evaluation," J Cataract Refract Surg, vol. 33, pp. 47-52, 2007.

Qiao, W. et al., "Bio-inspired accommodating fluidic intraocular lens," Opt Lett, vol. 34, pp. 3214-3216, 2009.

Koopmans, S.A. et al., "Accommodative lens refilling in rhesus monkeys," Invest Ophthalmol Vis Sci, vol. 47, pp. 2976-2984, 2006.

Nishi, O. et al., "Accommodation amplitude after lens-refilling with injectable silicone by sealing the capsule with a plug in primates," Arch Ophthalmol, vol. 116, pp. 1358-1361,1998.

Nishi, Y. et al., "Lens refilling to restore accommodation," J Cataract Refract Surg, vol. 35, pp. 374-382, 2009.

Kessler, J., "Experiments in refilling the lens," Arch Ophthalmol, vol. 71, 1964.

Koopmans, S.A. et al., "Polymer refilling of presbyopic human lenses in vitro restores theability to undergo accommodative changes," Invest Ophthalmol Vis Sci, vol. 44, pp. 250-257, 2003.

Nishi, O. et al., "Amplitudes of accommodation of primate lenses refulled withtwo types of inflatable endocapsular balloons," Arch Ophthalmol, vol. 111, pp. 1677-1684, 1993.

Burd, H. et al., "Numerical modeling of the accommodating lens," Vision Research, vol. 42, pp. 2235-2251, 2002.

* cited by examiner

ACCOMMODATING INTRAOCULAR LENS

STATEMENT AS TO RIGHTS TO INVENTIONS MADE UNDER FEDERALLY SPONSORED RESEARCH OR DEVELOPMENT

This invention was made with government support under EEC0310723 awarded by the National Science Foundation. The government has certain rights in the invention.

CROSS-REFERENCES TO RELATED APPLICATIONS

This application claims the benefit of U.S. Provisional Application No. 61/526,147, filed Aug. 22, 2011, and U.S. Provisional Application No. 61/488,964, filed May 23, 2011, which are hereby incorporated by reference in their entireties for all purposes.

BACKGROUND

1. Field of the Art

Embodiments of the present invention generally relate to surgically implanted eye prostheses, in particular, to microfabricated, fluid-filled intraocular lens devices.

2. Description of the Related Art

Surgical Procedure

An intraocular lens (IOL) can be used to replace a natural crystalline lens in human patients. Surgically replacing the crystalline lens includes making a main incision of approximately 2 to 4 millimeters (mm) in the periphery of the patient's cornea, cutting a 5.5 to 6 mm diameter circular hole in the eye's anterior capsule surrounding the lens, and removing the lens with phacoemulsification.

Because replacing the crystalline lens with an intraocular lens is an invasive procedure, this option is reserved for when vision is significantly impaired. Most commonly, it is used when the lens has become cataracted.

However, several factors are making this a less invasive procedure with faster recovery times. These include the trend of using smaller surgical instrumentation with a correspondingly smaller main incision to reduce postoperative recovery time and astigmatism. Furthermore, femtosecond pulse lasers are beginning to be used for lens/cataract removal, which makes the procedure safer, faster, and more accurate.

Surgical Complications

The most common surgical complication of lens replacement is posterior capsular opacification (PCOS), which occurs when residual lens epithelial cells move to the posterior portion of the capsule and proliferate. This makes the capsule hazy and creates visual disturbances. PCOS is treated by externally using a neodymium-doped yttrium aluminium garnet (Nd:YAG) laser to remove a circular section of the posterior capsule.

Intraocular lenses are often designed with a square edge to prevent lens epithelial cells from migrating to the posterior capsule, and therefore prevents PCOS.

Similar to posterior capsular opacification, anterior capsular opacification can also cause contraction of the lens capsule and visual opacification.

Accommodation and Presbyopia

"Accommodation" is where an eye changes optical power to focus on an object. This occurs from contraction of a ciliary muscle, which releases tension on the lens capsule. Upon release of this tension, the human lens naturally bulges out, increasing optical power.

Presbyopia is a clinical condition in which the eye can no longer focus on near objects. It is believed that this is a multifactorial process caused primarily by a loss of elasticity of the human lens. Therefore, replacing the human lens with an accommodating intraocular lens provides the capability to restore focusing ability and cure presbyopia.

Existing Devices

Current intraocular lenses can be categorized into three categories: monofocal, multifocal, and accommodating.

Monofocal lenses provide a single focal distance. Therefore, patients with a monofocal intraocular lens can no longer focus their eyes. This makes it difficult to focus on near objects.

To alleviate this condition, multifocal intraocular lenses were developed. Multifocal intraocular lenses provide simultaneous focus at both near and far distances. However, because of the unique optical design, patients may have a loss of sharpness of vision even when glasses are used. Patients can also experience visual disturbances such as halos or glare.

Accommodating intraocular lenses use the natural focusing ability of the eye to change the power of the intraocular lens. There are many designs of accommodating intraocular lenses, including single optics that translate along the visual axis of the eye to focus, dual optics that move two lenses closer and further apart, and curvature-changing lenses that change focal power by changing the curvature of the lens.

Future Market

Less invasive and faster surgical procedures in conjunction with accommodating intraocular lenses may allow intraocular lenses to be used for wider applications than are currently used today. This includes treatments for cataracts as well as presbyopia. This is a much larger market because almost all individuals undergo presbyopia around the fourth decade of life.

BRIEF SUMMARY

Systems, devices, and methods of the present application are related to an intraocular lens having one or more valve areas consisting of an elastomeric patch. The elastomeric patch is sized such that it self-seals after a needle puncture, such that the optically transparent fluid within the intraocular lens can be injected or withdrawn in order to adjust a lens after implantation. A slit can be manufactured into the patch that is sized for self-closing and allows standard gauge surgical needles to pass through. The patch can include a stepped area for additional closing power. The patch can be brightly colored so that it is more easily found by a surgeon. In another design, a wagon-wheel shaped valve with a plurality of wedge-shaped openings can be encapsulated in the walls of the lens. The center of the wagon wheel or each of the wedge-shaped openings can be pierced by a needle.

An intraocular lens can have a shape-memory alloy whose curvature can be wirelessly adjusted without later surgery. Air bubble-capture traps can be manufactured into the internal side of the lens in order to trap bubbles and hold them until a surgeon can remove them. A plurality of ports, such as the patches described above, can be placed so that multiple instruments can access the lens simultaneously. Markings on the side of the lens can indicate pressure or other stress in the lens.

Adhesive can be used to not only form a bond between an intraocular lens and the lens capsule but also placed to prevent cells from migrating to the optical center region of the lens.

Some embodiments of the present application are related to an intraocular lens apparatus. The lens apparatus includes a biocompatible polymer balloon fillable with an optically clear medium, the balloon configured for insertion into a capsular bag of an eye, and an elastomeric patch intimately attached to the balloon, the elastomeric membrane having a thickness sufficient self-sealing of needle punctures at nominal lens pressures.

The patch can have a thickness equal to or greater than 100 µm and or a thickness equal to or less than 700 µm, thereby being thin enough to avoid contact with a posterior iris when implanted in an eye. In some applications, the patch has a thickness between 160 µm and 350 µm, and in other application, the patch has a thickness between 150 µm and 250 µm.

The patch can be colored, and it can have a pre-formed slit (straight or with a stepped portion) adapted for a needle to pass through.

Some embodiments are related to an intraocular lens apparatus including a biocompatible polymer balloon fillable with an optically clear medium, the balloon configured for insertion into a capsular bag of an eye, and a shape memory alloy configured to be wirelessly modifiable by a remote source.

Some embodiments are related to an intraocular lens apparatus including a biocompatible polymer balloon fillable with an optically clear medium, the balloon configured for insertion into a capsular bag of an eye, and means for capturing air bubbles from inside the balloon, such as an out-pocket with a one-way valve and a port for admittance of a surgical instrument for removing air bubbles.

Some embodiments are related to an intraocular lens apparatus including a biocompatible polymer balloon, the balloon having a plurality of individually fillable compartments, each compartment fillable with an optically clear medium, the balloon configured for insertion into a capsular bag of an eye.

Some embodiments are related to an intraocular lens apparatus including a biocompatible polymer balloon fillable with an optically clear medium, the balloon configured for insertion into a capsular bag of an eye, and a plurality of ports attached to the balloon, the ports facilitating simultaneous entry into the balloon by a plurality of surgical injection devices.

Some embodiments are related to an intraocular lens apparatus including a biocompatible polymer balloon fillable with an optically clear medium, the balloon configured for insertion into a capsular bag of an eye, and a needle-pierceable port formed from a frame of material having a rigidity greater than that of the balloon, the frame encapsulated in place on a wall of the balloon by an envelope of polymer material affixed to the wall.

The frame can have a wagon-wheel configuration defining a plurality of wedge-shaped openings, each of which provides a needle-pierceable port. Alternately, the center of the wagon-wheel configuration can be pierced.

Some embodiments are related to an intraocular lens apparatus including a biocompatible polymer balloon fillable with an optically clear medium, the balloon configured for insertion into a capsular bag of an eye, the balloon having a plurality of circular or other pre-spaced markings thereon indicating an amount of flex and/or pressure within the balloon.

Some embodiments are related to a method of coupling an intraocular lens apparatus and a lens capsule. The method includes applying a circular annulus of adhesive, and implanting a lens apparatus such that the circular annulus of adhesive adheres the lens apparatus to a lens capsule, the circular annulus of adhesive forming a barrier to prevent migration of cells.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Figure 1:
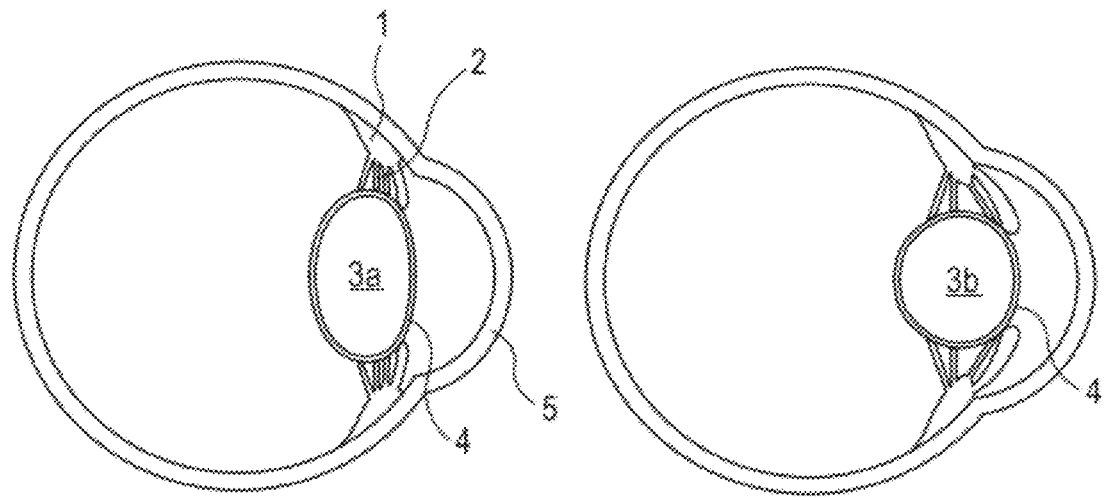
FIG. 1 is a cross section of a human eye in a non-accommodated (left side) and an accommodated state (right side).

An injectable accommodating intraocular lens system is disclosed as well as devices and systems relating thereto. In various embodiments, the lens is constructed to form a flexible, thin, biocompatible bag. During surgery, the bag is filled with an optically clear medium, such as silicone fluid. During insertion into the lens capsule of the eye, the intraocular lens has little or no medium in it in order to reduce its overall dimensions, allowing insertion through a small surgical incision. After insertion, the intraocular lens is inflated with the clear medium to a target dioptric power. Once inserted, the accommodating intraocular lens deforms in response to the natural focusing mechanism of the existing ciliary muscle to change focus in a manner similar to a human lens.

Because of its ability to fit through small incisions, the injectable accommodating intraocular lens can be used with minimally invasive surgical techniques, making recovery time for a patient more rapid and reducing surgical complications. A minimally invasive surgical procedure, resulting in an ability of the intraocular lens to accommodate, makes this device well suited not only to fix cataracts, but also for other less serious conditions such as presbyopia.

The Bag

The bag of the injectable accommodating intraocular lens is typically made of an optically clear flexible material. This allows it to be deformed by contraction and relaxing of ciliary muscles during accommodation. However, other biocompatible materials may also or alternatively be used. In some embodiments, the bag consists of a biocompatible polymer, for example, a parylene, acrylic, and/or silicone elastomer.

In some embodiments, the bag comprises a composite of more than one material layered on top of another, for example, parylene coating a silicone elastomer. A composite structure can be used to alter the flexing properties of the lens, improve stability of the materials, and prevent lens epithelial cells from traveling across the intraocular lens.

Parylene and silicone bags in accordance herewith may be under 100 micrometers (μm) in thickness, and in some embodiments under 10 μm. Parylene bags under 10 μm in thickness have been found to be effective, and silicone bags under 40 μm have been found to be effective.

For compatibility with subsequent ocular procedures, the bag and optically clear medium are constructed of materials that are not damaged by a Nd:YAG laser. Furthermore, the materials used along the visual axis of the device, such as parylene, desirably are stable—despite light exposure for decades—and do not change color over time.

When inserted and inflated, the bag is mechanically coupled to the lens capsule in order to accommodate when the ciliary muscles contract. The coupling occurs at the periphery of the lens. This allows the device to function after both anterior and posterior capsulotomies have been performed.

In operation within the eye, ciliary muscles contract and relax, causing the capsule diameter to decrease and increase. In a manner similar to the intact human crystalline lens, the lens capsule then transmits this force to the prosthetic accommodative intraocular lens. As the diameter of the capsule decreases, the anterior and posterior surfaces of the lens round, decreasing their radius of curvature, and in turn increasing the power of the lens.

To prevent anterior or posterior capsular opacification, a circumferential square-edge protrusion is made around the periphery of the lens at the posterior and/or anterior side in order to prevent migration of lens epithelial cells along the surface of the capsule. In some implementations, a protrusion is made around the periphery of the lens at the anterior side. The anterior ridge is particularly important for surgical cases when only a small capsulotomy is performed because lens epithelial cells may migrate to the anterior surface of the capsule causing visual disturbances. These square edges contact the lens capsule, inducing strain and a continuous circumferential angular discontinuity, which forms a barrier preventing lens epithelial cells from migrating from the periphery to the optical axis.

In one implementation, the bag is made from a material with a higher index of refraction than the optically clear medium. The two materials form a single lens with a variable index of refraction, similar to a gradient index (GRIN) lens. Two exemplary materials for this implementation are parylene with a refractive index of 1.6 and silicone fluid with an index of 1.4. Different indexes of refraction for the bag and optically clear medium form a single lens with a variable index of refraction.

In one implementation, a shape memory alloy, such as nickel titanium (Nitinol), is used to non-invasively adjust the power of the lens. The shape memory alloy is integrated into the lens. When the shape memory alloy changes shape, it causes the lens deform, therefore changing dioptric power. The shape memory alloy is actuated with a remote source, such as a radio frequency (RF) transmitter. Therefore, no surgically invasive procedure is required to modify the power of the lens after implantation.

Air Bubble Capture

One implementation of an intraocular lens device has a feature that facilitates capture of air bubbles. This feature is typically located along the periphery of the lens. One example of this is a narrow inlet that expands into a larger out-pocket. Once an air bubble travels through the inlet, it is caught in the larger out-pocket. Exemplary profiles of the out-pocket include a simple chamber or a maze. Furthermore, certain implementations of the lens have a one-way valve, for example a flap valve, which allows the air bubble into an out-pocket but prevents it from escaping. Any residual air bubbles that have not been removed are then positioned and captured.

One implementation of an intraocular lens device contains a section of the lens that naturally allows an air bubble to diffuse through. This section may be located along the superior aspect of the lens or along the periphery of an air-bubble capture feature.

One implementation of an intraocular lens device contains a section of the lens that interacts with an instrument to allow surgical removal of the air bubble. The instrument either pierces the periphery of the lens to remove the air bubble or causes the air bubble to diffuse through the lens wall. The air bubble may diffuse across the wall of the lens if vacuum is locally applied externally. It is generally preferable to remove air bubbles during the surgical implant procedure.

Optically Clear Medium

The intraocular lens bag can be filled with an optically clear medium with an index of refraction higher than the surrounding aqueous humor and vitreous. A low viscosity silicone fluid or hydrogel may be used, for example. A low viscosity silicone fluid not only allows the lens to respond quickly to changes in the ciliary muscle, but also allows rapid injection through small diameter hypodermic needles. The use of a hydrogel or equivalent material allows tuning of the bulk modulus of the lens for optimal accommodative amplitude. Although hydrogel is used as an exemplary material, equivalent materials can be used.

In one intraocular lens implementation, the optically clear medium is used to change the refractive power of the lens. This is accomplished by changing the ratio of fluids in the lens. It can also be accomplished by using a medium having a tunable refractive index. In the former case, as the lens is filled it changes shape, and therefore optical power. In the latter case, the lens power is modified by adding or exchanging fluid with a different refractive index or changing the refractive index of the medium itself. As an example, changing the concentration of a dissolved solute or percentage of nanocomposite in the medium can change the refractive index of the fluid and hence the dioptric power of the lens. This approach can be used to adjust optical power during the initial procedure as well as after surgery, for example to adjust for visual changes.

If desired, a blue blocking capability may be added to the lens. For example, a colored biocompatible polymer that absorbs harmful blue or small wavelengths of light can be added. The balloon can attenuate ultraviolet A or B rays. In addition, blue blocking and ultraviolet A and/or B blocking capability can be added to the fluid filling the lens.

In addition, pharmaceuticals can be added to the optically clear medium for intraocular delivery over an extended period of time. Refilling can occur through the injection site.

Injection Site

The optically clear medium can be injected into the intraocular lens through an injection site. After optically clear medium has been injected into the lens, the injection site seals to prevent fluid leakage. For a single sealing design, sealing can be accomplished by injecting through a thin hollow tube attached to the lens. After injection, the tube is welded closed with local heat using a hot microtweezers or an equivalent micro device for safe intraocular use. Any peripheral residue of the tube is then removed from the surgical site. For multiple uses or fine adjustment of the lens, a reusable fill/discharge port can be made on the side of the lens bag. A hypodermic needle can pass through the port and inflate or deflate the lens accordingly.

One implementation of the injection site on the intraocular lens has a reusable fill-discharge port that is surgically accessible during insertion and adjustment, but it is moved peripherally off the optical axis once filling is complete to prevent visual disturbances. The injection site can be moved peripherally off the central 4.25 mm diameter of the lens. Preferably, the injection site is moved peripherally outside the center 6 mm diameter of the lens.

To avoid any potential damage to surrounding tissue from heat, alternate implementations of the injection site can use a self-sealing elastomer. During injection of the optically clear medium, a hollow tube, such as a small hypodermic needle, is used to pierce a slot in the elastomer membrane. During this process, the elastomer deforms away from the hypodermic needle. Next, the hollow tube slides through the incision. After injection of the fluid, the tube is removed and the elastomer retracts to its original position, sealing the incision. The thickness of the elastomer is determined by the amount of pressure in the lens and the injection diameter. The membrane can be equal to or greater than 100 µm and less than or equal to 700 µm. In some embodiments, a range of between 160 µm and 350 µm is optimal. In other embodiments, a range of between 150 µm and 250 µm is optimal.

Optimally, the thickness should be thin enough to avoid contact with the surrounding tissue such as the iris, zonules, or ciliary muscle. In particular, it should be thin enough to avoid contact with the posterior iris. Clinically contact with this can cause a series of medical conditions including glaucoma or uveitis-glaucoma-hyphema (UGH) syndrome.

To prevent lateral movement of the injection tube during insertion, the elastomer injection site may be coated on one or both sides with a stiffer material, such as parylene. The stiffer material serves as a rigid guide for the injection tube, while the elastomer is used to seal the incision once the injection tube is removed. In one implementation, a guide for the injection needle is used to allow the needle to penetrate the same injection site multiple times. Multiple injections might be used for adjusting the base power of the lens after it has been placed in the same or subsequent surgical procedures.

One implementation of the injectable intraocular lens utilizes two injection sites. One injection site is used to infuse the optically clear medium, and the other site is used to aspirate the medium. Recirculation of the optically clear medium can be employed to remove unwanted debris or small air bubbles. It can also be used when exchanging a fluid of one index of refraction with another fluid of different index of refraction.

Surgical Procedure

A compact cross section of the inflatable intraocular lens allows less invasive procedures than traditional surgical methods. One method of performing the a lens extraction can involve using a femtosecond laser to create a main incision, lens sectioning, and a small capsulotomy of 1 to 2 mm in diameter. The crystalline lens is aspirated or emulsified out of the opening and the intraocular lens is then injected. The capsule is maintained intact to provide a good mechanical coupling between the capsule and the lens.

After insertion of the intraocular lens, it is filled with an optically clear medium. The dioptric power of the lens may be varied by adjusting the index of refraction of the medium, the amount of medium injected into the lens, a combination of these two parameters, or otherwise. Individually fillable compartments in the lens can separately store fluids with different indexes of refraction. The volume of fluid in each of the departments can determine the combined dioptric power. The dioptric power of the lens can be determined before surgery, or monitored and adjusted during the surgical procedure. Furthermore, dioptric power can be adjusted post-surgery after the surgical incisions have healed or monitored on a temporal basis and adjusted. In one implementation, post-surgical adjustment of power involves entering the eye with a small-diameter hypodermic needle, cannula, or similar device, and then inserting an injection system into the injection site. In one implementation, a 30-gauge cannula or smaller is used to enter the eye, the injection system is inserted through the cannula, and then inserted into the injection site. In other implementations, a remote source, such as a radio-frequency source, is used to adjust the profile of a shape memory alloy embedded in the lens to change the dioptric power of the lens.

Markings on Lens

In certain configurations, an intraocular lens has a series of markings on its anterior or posterior surface. The markings can be circular in shape. Deformation of the markings can indicate a shape change of a particular portion of the lens. Clinically this can be used to measure the amount of dioptric power in the lens. After implantation of the device, a clinician can visually observes the change in the marking to monitor the level of accommodation of the lens. In addition, the markings can be used to measure base power of the lens.

In certain renditions of the lens, the markings are used to monitor intraocular pressure in a non-contact manner. Clinically this can be used for monitoring glaucoma patients.

Fixing the Lens to the Lens Capsule

In certain embodiments of the invention, a portion of the lens can be glued or otherwise adhered to lens capsule. In an exemplary embodiment, the anterior portion of the lens is glued to the periphery of the anterior capsulorhexis. When glued to the lens capsule, the lens forms a rigid connection with the capsule, allowing it to deform in a physiologically similar manner to the original lens. In addition, the adhesive prevents cells, such as lens epithelial cells, from migrating across the capsulorhexis. With an anterior capsulorhexis, the lens cells are prevented from creating opacification or visual disturbances to the anterior surface of the lens.

Adhesives can include temperature-responsive polymers, such as poly (N-isopropylacrylamide). The adhesive can be applied manually after the lens is placed or be previously mounted on the lens. In one embodiment of the invention, the adhesive is mounted on the lens in a circular annulus on the posterior and anterior surface of the lens. Upon injection and inflation of the lens, the adhesive sets, forming a seal along the optical axis of the eye. The seal can be 4.5 mm in diameter. Any residual cells in the equatorial region of the lens capsule can be prevented from migrating across the glued areas, thereby preventing opacification of the intraocular lens or the lens capsule.

FIGURES

FIG. 1 is a cross section of a human eye in a non-accommodated (left side) and an accommodated state (right side). The normal physiology of the eye allows accommodation of crystalline non-accommodated lens 3a by contraction of ciliary muscle 1, which releases tension on zonules 2 and causes a rounding of the lens to accommodated lens 3b. The lens is surrounded by capsule 4, which transmits the force from the zonules to the lens itself.

Figure 2:
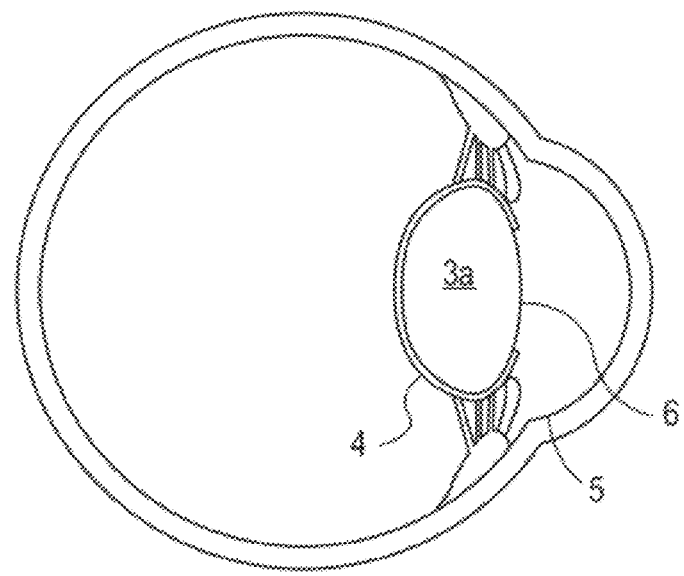
FIG. 2 is a cross section of a human eye with a traditional capsulotomy of the prior art.

FIG. 2 is a cross section of a human eye with a traditional capsulotomy. The surgical procedure of removing crystalline lens 3a and inserting an intraocular lens typically begins with cutting a main incision on the periphery of cornea 5. Next, a circular hole, known as a "capsulotomy" is cut with a diameter of approximately 5.5 mm in the anterior, central portion of lens capsule 6. This hole provides surgical access to lens 3a, which is then removed.

Unfortunately, the capsulotomy typically damages the integrity of lens capsule 4 and hinders its ability to fully transmit forces to the implanted lens. Integrity of the lens capsule is especially important for an accommodating intraocular lens, which often requires a strong mechanical coupling between the intraocular lens and the lens capsule.

Figure 3:
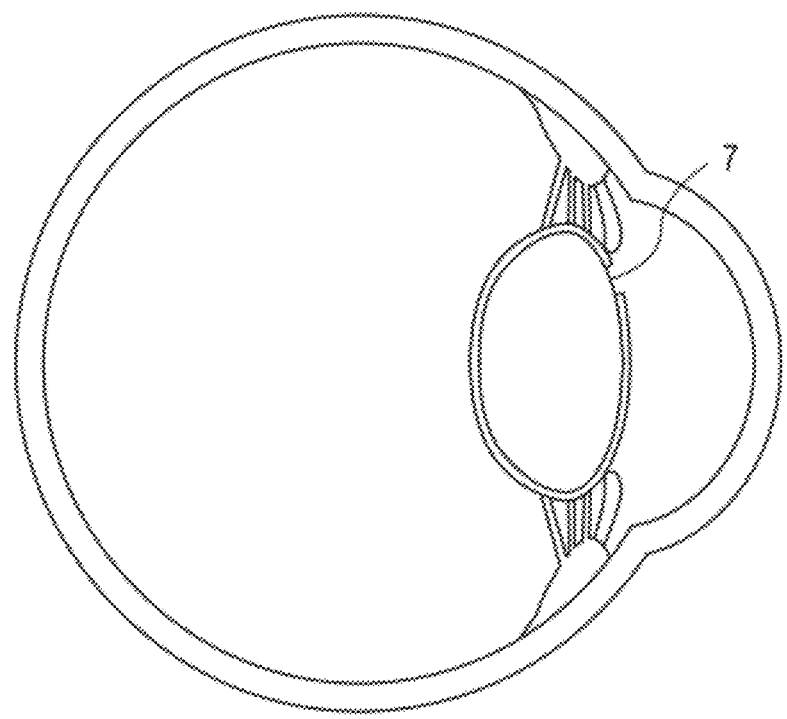
FIG. 3 is a cross section of a human eye with a minimally invasive peripheral capsulotomy in accordance with an embodiment.

FIG. 3 is a cross section of a human eye with a minimally invasive peripheral capsulotomy in accordance with an embodiment. A small peripheral capsulotomy of less than 3 mm in diameter is made in the lens capsule, and the crystalline lens is extracted from the small incision. In one embodiment, peripheral incision 7 is less than 2 mm in diameter.

Figure 4:
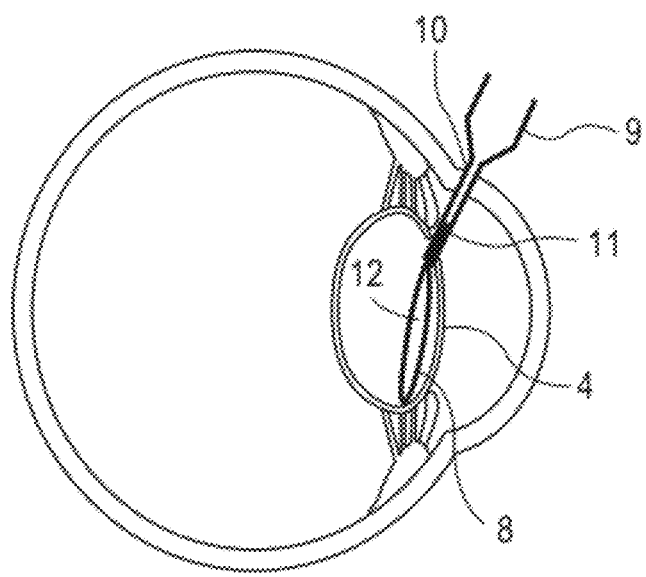
FIG. 4 is a cross section of a human eye with an injectable accommodating intraocular lens being injected into the capsule in accordance with an embodiment.

FIG. 4 shows an injectable, accommodating intraocular lens 8 being inserted into the lens capsule through a small peripheral incision, after the crystalline lens 3a has been surgically removed. The distal end of the insertion device 9 is first inserted through the main surgical incision 10 and then inside the lens capsule 4 through a small peripheral incision. Insertion device 9 has a narrow tube on its distal end. The narrow tube has an outer diameter smaller than the diameter of the peripheral incision, for example, less than 2 mm. The inner diameter of the insertion device is large enough to allow uninflated lens 8 to pass through without damaging the lens. During injection, the interior portion 12 of the injectable accommodating intraocular lens has little or no fluid in it so it can pass through insertion device 9.

Although FIG. 4 shows the lens inserted through a peripheral incision 7, it can be used with other incisions such as the traditional capsulotomy 6 shown in FIG. 2.

Figure 5:
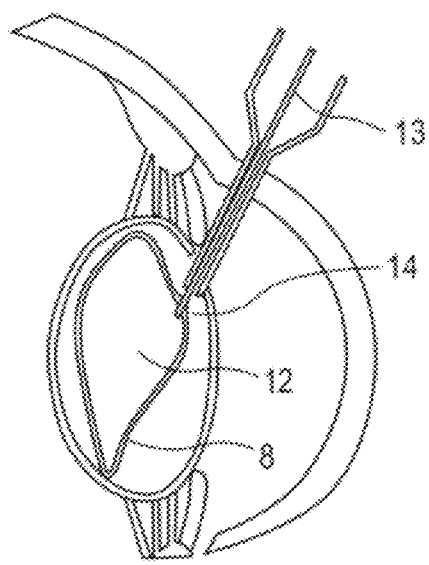
FIG. 5 is a cross section of a human eye with an injectable accommodating intraocular lens being inflated with an optically clear medium inside the capsule in accordance with an embodiment.

FIG. 5 shows injectable accommodating intraocular lens 8 being inflated with an optically clear medium. The medium passes from an infusion source on the proximal end of the fluid injector 13 through the fluid injector, into interior portion 12 of intraocular lens 8.

The fluid injector passes into lens 8 through injection site 14, which is sealed after fluid injector 13 is removed. The method of sealing can be from the relaxation of an elastomer membrane such as silicone, from external sealing such as gluing or cautery, or otherwise.

In one embodiment the optically clear medium is a low viscosity silicone fluid, for example, 100 centistokes, and fluid injector 13 is attached to lens 8 before insertion of the lens. In this implementation, the lens 8 is inserted, and then immediately filled with the same tool.

Figure 6:
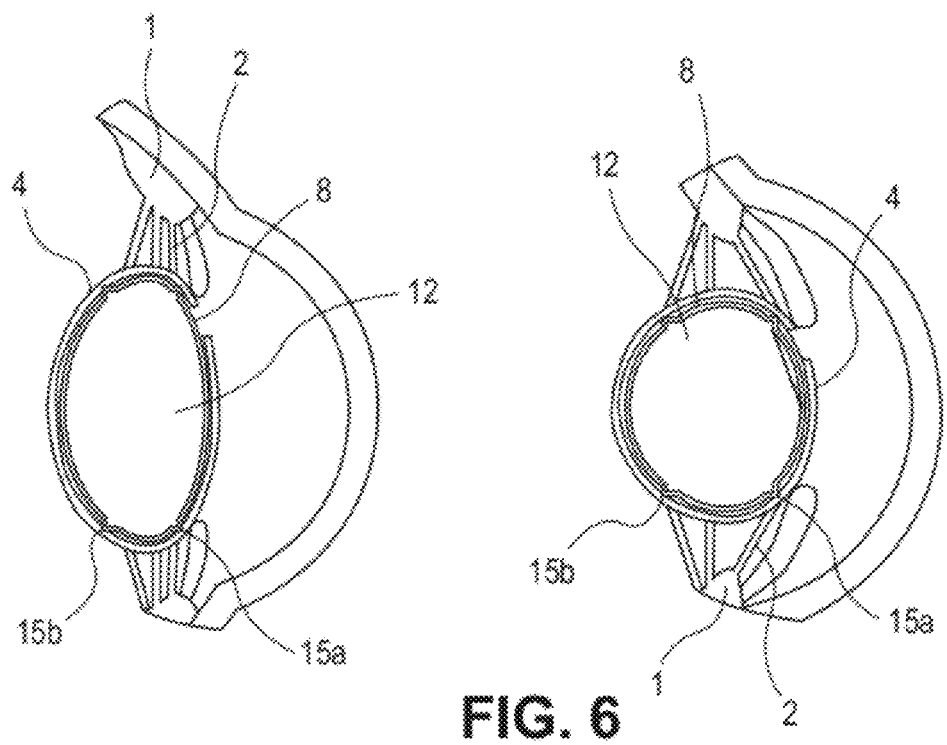
FIG. 6 is a cross section of a human eye with a peripheral incision and an injectable accommodating intraocular lens inserted into the lens capsule in a non-accommodated (left side) and an accommodated state (right side) state in accordance with an embodiment.

FIG. 6 is a cross section of a human eye with a peripheral incision and an injectable accommodating intraocular lens inserted into the lens capsule in a non-accommodated (left side) and an accommodated state (right side) state. Lens 8 is filled to a base dioptric power with the optically clear medium in central portion 12. On the left side of the figure, the injectable accommodating intraocular lens 8 is in the unaccommodated, or non-accommodated state. On the right hand side of the figure the lens is in the accommodated state. Similar to the physiology of a healthy human lens, ciliary muscle 1 contracts, releasing tension on zonules 2 causing deformation of lens capsule 4 and lens 8 to round and change dioptric power. Lens 8 is in direct contact with the capsule 4, and this mechanical connection is typically required for lens 8 to change shape with the capsule.

The edge of the lens 8 fits tightly against lens capsule 4, providing a seal that prevents lens epithelial cells from migrating and causing posterior or anterior capsular opacification.

An implementation uses circular anterior lens protrusions 15a along the anterior portion of the lens and circular posterior lens protrusions 15b along the posterior portion of the lens to form circular ridges. The ridges cause an angular discontinuity in the lens capsule 4. This provides a barrier on the anterior and posterior surface of the capsule and lens, preventing equatorial lens epithelial cells from migrating to the center of lens capsule 4 or intraocular lens 8. In the exemplary embodiment, the ridges are set at a diameter larger than 4.25 mm stay out of the optical path of the lens/eye. This can prevent light scattering in the eye and subsequent visual disturbances.

Figure 7:
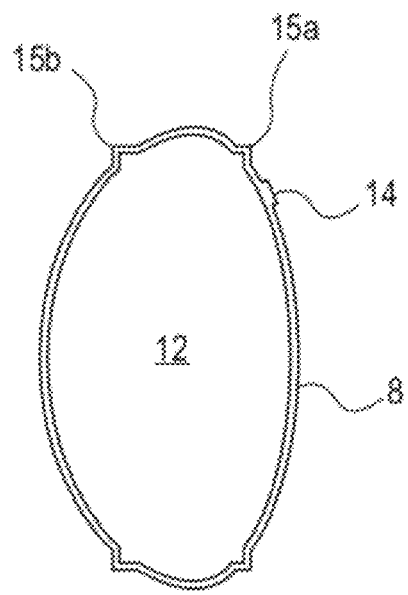
FIG. 7 is an injectable accommodating intraocular lens in accordance with an embodiment.

FIG. 7 is an injectable accommodating intraocular lens in accordance with an embodiment. Lens 8 is shown with central portion 12 filled with an optically clear medium. Injection valve 14 is shown in the periphery of the lens to prevent light scattering from the central portion of the lens. However, its placement is far enough from the periphery to allow surgical access through the dilated pupil. In one implementation, the injection valve is filled while it is surgically accessible and then moved peripherally away from the optical axis of the eye. Upon subsequent procedures for injection or removal of fluid, the valve is surgically moved towards the optical axis, fluid is injected or removed, and the valve is moved peripherally again. Anterior and posterior protrusions 15a and 15b are shown as well.

Similar to the human lens, this lens has multiple indices of refraction, similar to a gradient index (GRIN) lens. More specifically, the polymer shell of lens 8 may have a higher or lower index of refraction than the optically clear fluid inside.

Figure 8:
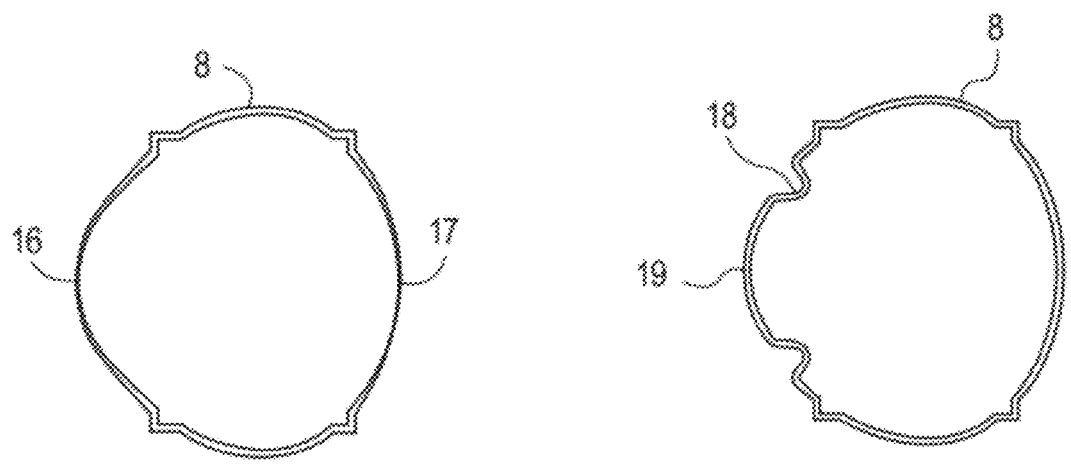
FIG. 8 is the injectable accommodating intraocular lens with a flexible central portion in accordance with an embodiment.

FIG. 8 shows one embodiment of lens 8 with a central portion of the optic that is more flexible than the peripheral portions of the lens. In this figure, the central portion of the lens is thinned on the anterior side of the lens 16 and the posterior side of the lens 17 to increase flexibility. When the lens flexes during accommodation, the posterior central portion 16 and anterior central portion 17 of the lens flex more than other portions of the lens, amplifying the total curvature change and dioptric power change in the center of the lens. The central flexible portions 16 and 17 of the lens are less than 5 mm in diameter, and preferably about 3 mm in diameter.

Although the left side of FIG. 8 shows the central flexible portions of the lens as a thinned portion of the lens, one skilled in the art will recognize there are many methods to make the central portion more flexible. These include but are not limited to using two materials for the lens with the more flexible material used for the central portion of the lens. Alternatively, as shown on the right side of FIG. 8, hinged portion 18 of the lens can be used to cause central portion 19 between the hinges of the lens to preferentially flex. The hinged portion 18 can be located outside the visual axis of the lens to prevent visual disturbances, and preferably has a diameter of 4.25 mm or larger.

Although the illustrative embodiments of the invention shown in FIG. 8 are flexible on one side, one skilled in the art will recognize that any of the designs can be modified so the flexible portion of the lens is solely on the anterior, solely on the posterior, or on both sides of the lens.

One implementation of the injectable accommodating intraocular lens has multiple compartments that are individually filled. By differentially filling the compartments, the curvature of the lens can correct for aberrations in the optical system of the eye such as astigmatism.

Figure 9:
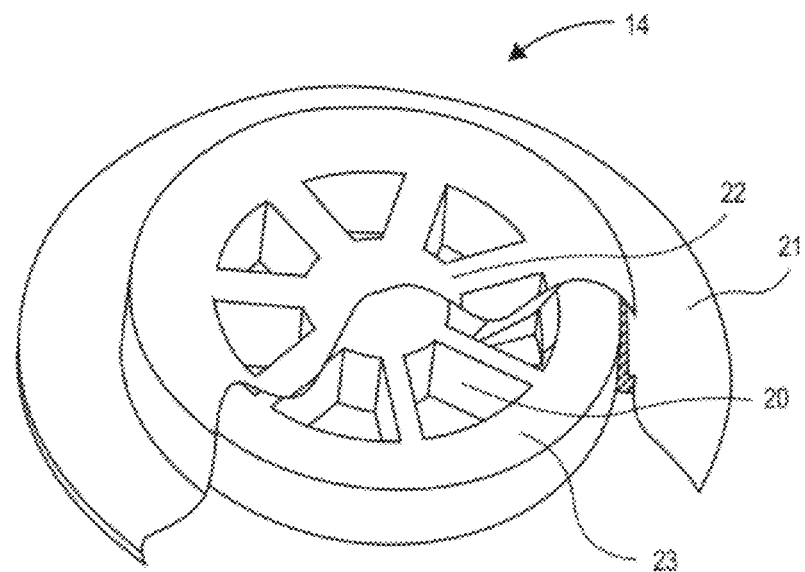
FIG. 9 illustrates a wagon wheel-shaped frame port having needle-pierceable portions in accordance with an embodiment.

FIG. 9 shows an embodiment of injection valve 14 that utilizes a wagon wheel-shaped frame of stretchable elastomer 20 (e.g., silicone) surrounded by supporting polymer 21 (e.g., parylene). This can be useful where two materials such as silicone and parylene do not adhere well to one another. Valve 14 has central portion 22 and peripheral portion 23. Supporting polymer 21 surrounds and envelopes the frame on all sides, encapsulating the frame and providing strength to prevent lateral tearing of the stretchable polymer 20. Central section 22 in the wagon wheel-shaped frame can be pierced by a needle and/or the wedge-shaped sections can be pierced to provide ports to the inside of the intraocular lens. Different shapes without spokes are contemplated. Alternatively, it is possible to use a stretchable elastomer coated with support polymer only on one side, with or without a central clearing in the support polymer.

A self-sealing valve can consist of a stretchable elastomer. Once a fluid injector is retracted from the stretchable elastomer, the latter self-seals, preventing leakage from the lens.

The thickness of a stretchable elastomer required to self-seal itself depends on the diameter of the fluid injector, the geometry of the stretchable elastomer, etc.

Figure 10:
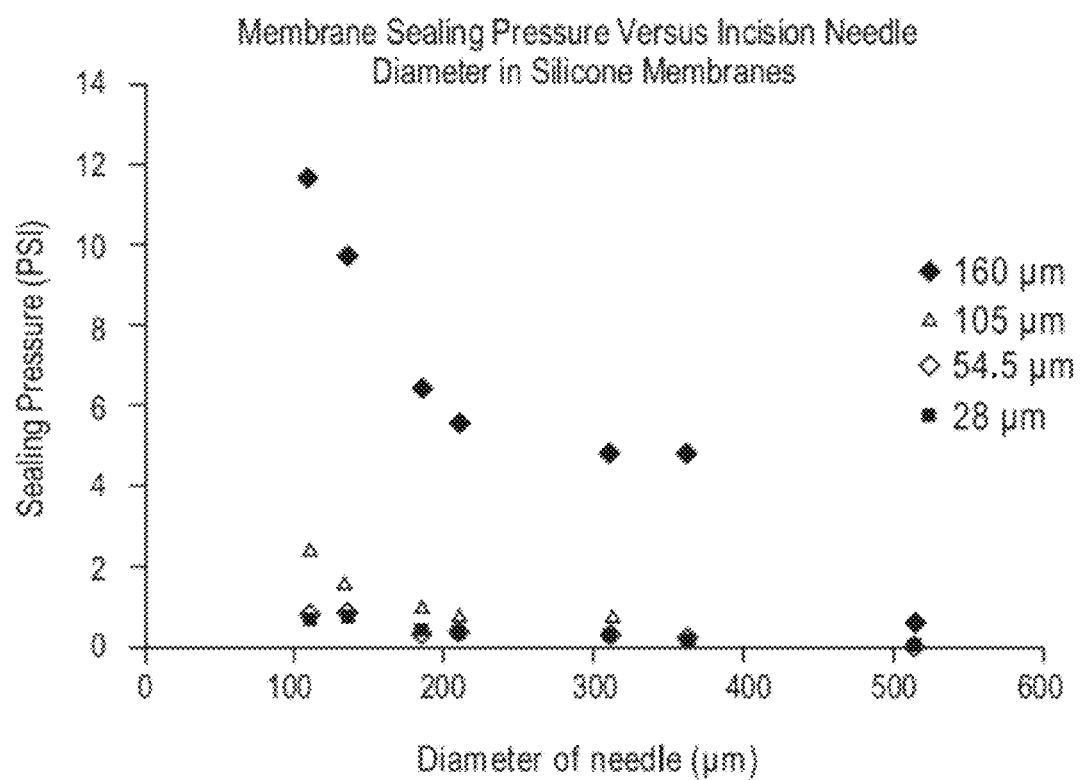
FIG. 10 is a chart illustrating experimentally determined thicknesses of a valves that self-seal the lens at different pressures.

FIG. 10 is a chart illustrating experimentally determined thicknesses of a valves that self-seal the lens at different pressures. In the figure, data is charted from thin membrane seal testing with air on one side and water on the other side. A thin silicone elastomer membrane was sealed across a 1/16 inch diameter hole. Different diameter size hypodermic needles were used to pierce the center of the membrane. Next, a pressure differential was applied across the membrane and leakage of air was visually observed. The sealing pressure was defined as the pressure required for air to leak through the incision in the silicone membrane.

If a hypodermic needle is used, data similar to that of FIG. 10 can be used to pick the correct seal thickness for a given incision diameter. For example, if the membrane is circular and has a diameter of 1/16 inch, then for a 110 μm diameter needle to seal more than 2 psi air, the membrane thickness of 105 μm or more should be used.

The surgical time for lens removal and replacement is short and is often less than fifteen minutes. This is beneficial because faster procedures reduce postoperative complications, reduce overall procedure cost, and lower surgeon fatigue. Because the intraocular lens requires filling during the operation, it is important to reduce the overall filling time. In one embodiment, the lens system is intended to be filled in less than 60 seconds, for example, less than 20 seconds.

The speed at which the injectable accommodative intraocular lens is filled with fluid depends on the volume of the lens, the pressure differential being used to push the fluid through the fluid injector, the viscosity of the fluid, the geometry of the fluid injector, etc.

Figure 11:
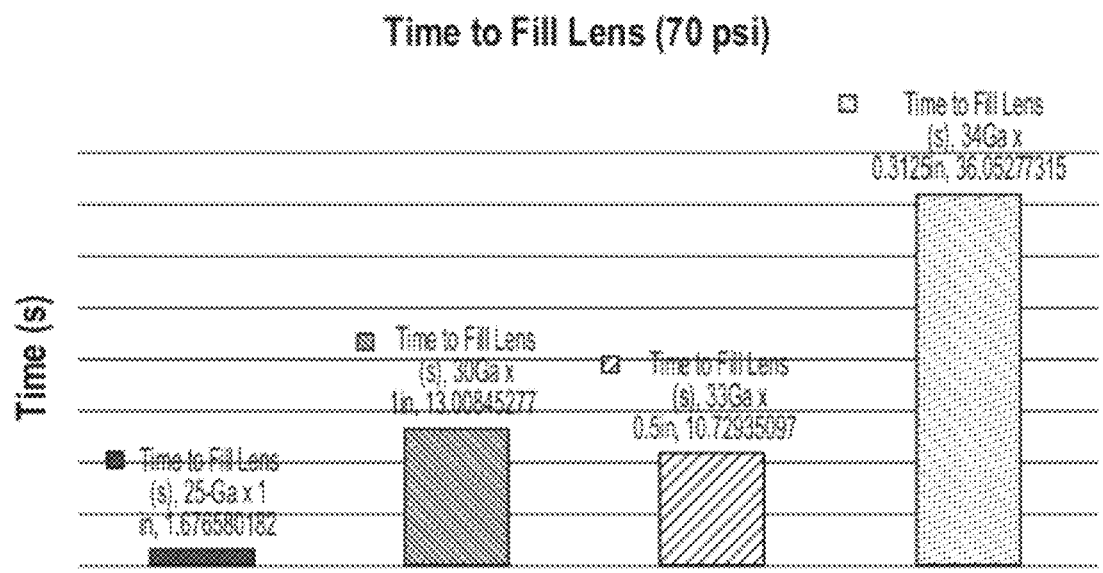
FIG. 11 is a chart illustrating needle diameters found to fill injectable accommodating intraocular lenses in a specific amount of time.

FIG. 11 is a chart illustrating commercially available hypodermic needle diameters found to fill injectable accommodating intraocular lenses in a specific amount of time. For the tests, 20 centistokes silicone fluid was used. The data is reported as the time (in seconds) to fill a human lens, which was estimated to have a volume of 160 $mm^3$ with a driving pressure of 70 psi. Based on the sample data in FIG. 11, the geometries of the 25 Ga, 30 Ga, and 33 Ga hypodermic needles would all be acceptable for injection of the 20 centistokes fluid at 70 psi, while the 34-Ga needle geometry would not be acceptable because it requires over 20 seconds to fill.

A few methods of manufacturing the injectable accommodating intraocular lens are described for illustrative purposes. In one method, the lens shape is molded with a dissolvable material, such as a wax. Chemical vapor deposition of parylene is performed on the wax mold, making the shape of the lens. During the deposition process, the surface finish of the deposited material can be made smoother by using a light coating of a liquid to wet the surface of the wax mold. For example, dipping the wax mold in a polydimethylsiloxane (PDMS) fluid before deposition fills in slight surface roughness from the wax mold, creating a better optical surface for the lens.

Figure 12:
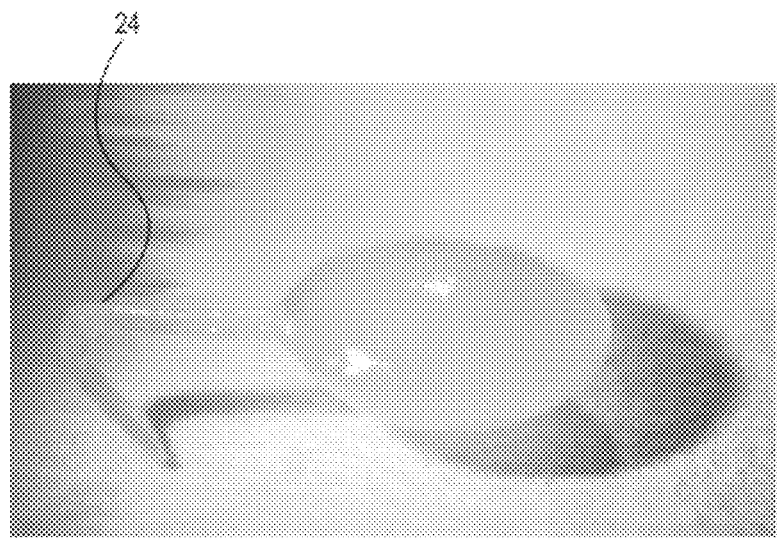
FIG. 12 is a picture of a lens with an injection tube before dissolvable mold material has been removed in accordance with an embodiment.

FIG. 12 is a picture of a lens with an injection tube before dissolvable mold material has been removed in accordance with an embodiment. The wax mold is either supported by injection tube 24 or by a small needle. A silicone elastomer valve is placed on the side, either by placing a small drop of silicone elastomer and curing or by placing a cured silicone elastomer valve on the deposited parylene. A second chemical deposition of parylene is performed to encapsulate the valve. If an injection tube is used, it is then cut open distally from the lens, and the wax mold is dissolved out of the lens. The tube can be sealed by cautery or glue after dissolving the wax.

Figure 13:
FIG. 13 is a close-up picture of a 1.5 µm thick parylene lens with its injection system cauterized in accordance with an embodiment.

FIG. 13 is a close-up picture of a 1.5 μm thick parylene lens with its injection system cauterized at 25 in accordance with an embodiment.

Alternatively, a single chemical vapor deposition can be performed on the wax mold with the injection tube. A fluid injector is used to inject into the injection tube during insertion of the lens. When the lens is filled, the fluid injector is removed and the injection tube is closed off with cautery, glue, or other similar method and potentially cut off.

Figure 14:
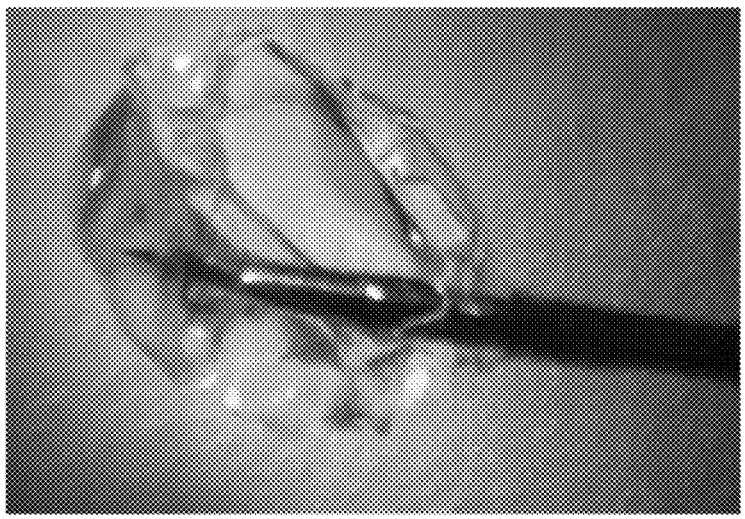
FIG. 14 is a picture of a lens with mold material dissolved and an injection system attached in accordance with an embodiment.

FIG. 14 is a picture of a lens with mold material dissolved and an injection system attached in accordance with an embodiment.

Likewise, parylene deposition can be done on the lens while it is either rolled, or levitated in the chemical deposition chamber. Next, the stretchable elastomer patch is placed on the deposited parylene, and a second parylene deposition is performed in a similar manner. Finally, the patch valve is opened by inserting the fluid injector or other instrument into the interior of the lens and the molding material is dissolved out.

Figure 15:
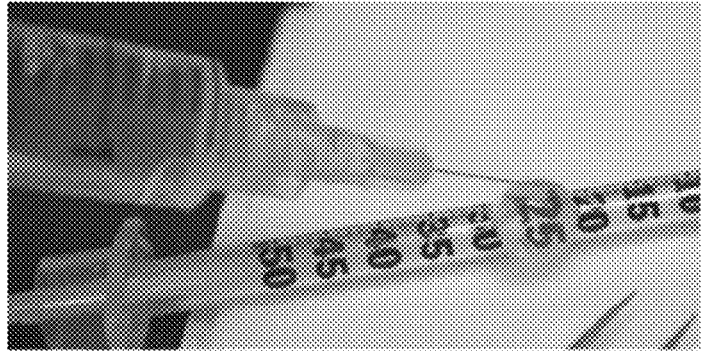
FIG. 15 is a picture of a parylene lens filled with 20 centistoke silicone fluid in accordance with an embodiment.

FIG. 15 is a picture of a parylene lens filled with 20 centistoke silicone fluid in accordance with an embodiment.

Figure 16:
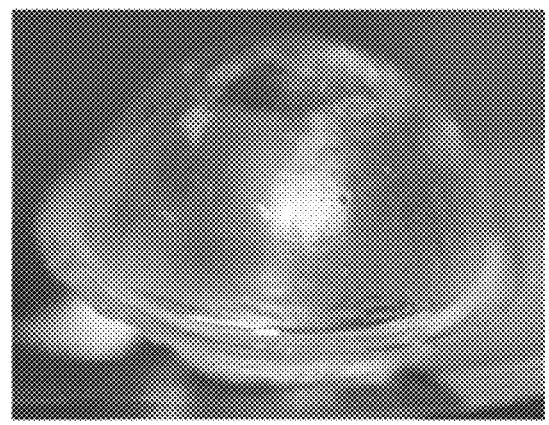
FIG. 16 is a picture of an exemplary composite parylene-on-silicone lens in accordance with an embodiment.

FIG. 16 shows an exemplary composite parylene on silicone lens. A 40-μm thick silicone lens was spin coated, and an injection site was molded to the lens. Next, the silicone surface was modified with reactive oxygen ions and then silanization to increase adhesion with parylene. Parylene was then deposited on the lens. The peripheral parylene was etched away with oxygen plasma, leaving a silicone lens covered with parylene along the central optical axis. A circular ring at the top of the image indicates the border of the parylene/silicone composite and the peripheral silicone.

Figure 17:
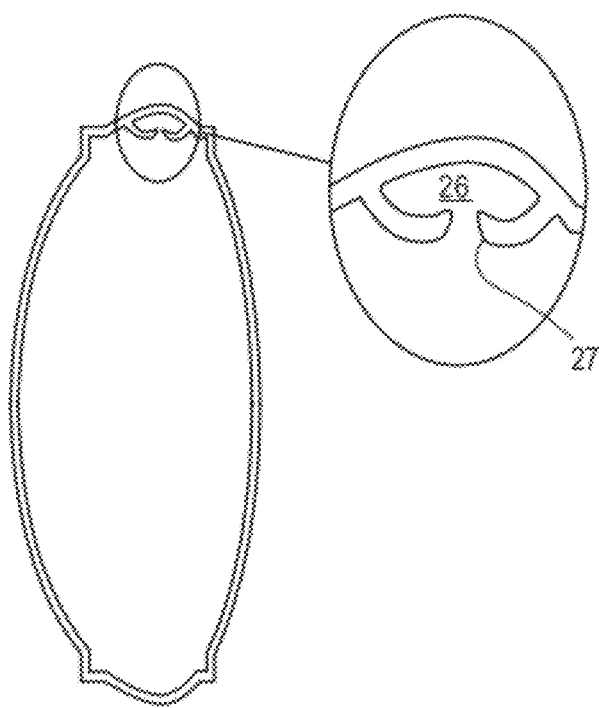
FIG. 17 illustrates an exemplary air bubble capture mechanism in accordance with an embodiment.

FIG. 17 shows an exemplary air bubble-capture mechanism. Once air bubbles travel through inlet and one-way valve 27, they are captured in out pocket 26 area. Although the profile of the inlet 27 allows air bubbles to be captured easily, the profile of out-pocket 26 makes it difficult for the air bubble to return into the main body of the lens.

Figure 18:
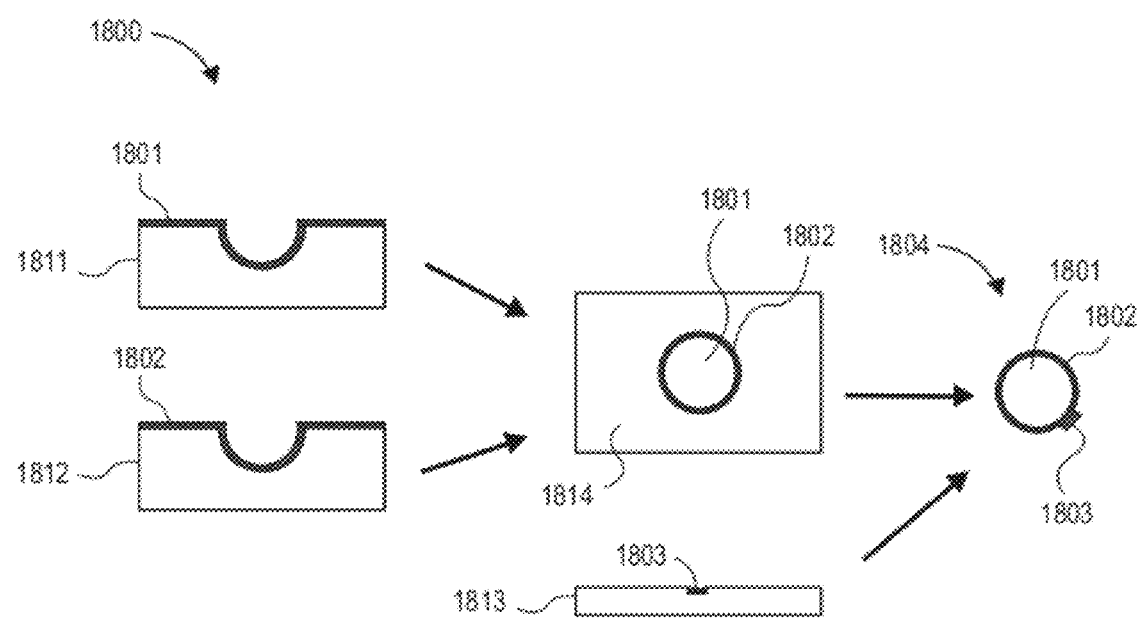
FIG. 18 illustrates a silicone intraocular lens manufacturing process using molds in accordance with an embodiment.

FIG. 18 illustrates a silicone intraocular lens manufacturing process using molds in accordance with an embodiment. A silicone elastomer such as NuSil MED4-4210 can be used to mimic the Young's modulus of a human lens capsule. In this case, the Young's modules of silicone is 1 MPa as compared with 1.5-6 MPa in a natural human lens. A capsular thickness of 30 μm is formed in silicone as compared with 3-21 μm in a natural human lens.

In manufacturing process 1800, the lens body is fabricated by spin coating silicone elastomer 1801 and 1802 on molds 1811 and 1812, respectively. One mold corresponds to the anterior half of the lens; the other mold corresponds to the posterior half of the lens.

After spin coating, the two halfs 1801 and 1802 are clamped and fused together in device 1814 and placed in a convection oven to cure.

Microelectromechanical systems (MEMS) refill valve 1803 is fabricated by molding a colored silicone patch in a 250 μm thick SU8-100 mold 1813. Patch 1803 is peeled from the mold and attached to lens 1804 using adhesive to anterior segment 1801 of the lens. After attaching the MEMS refill valve to the lens, an incision is made in the refill valve to allow silicone oil to be injected into the body of the lens after surgical implantation.

Figure 19A:
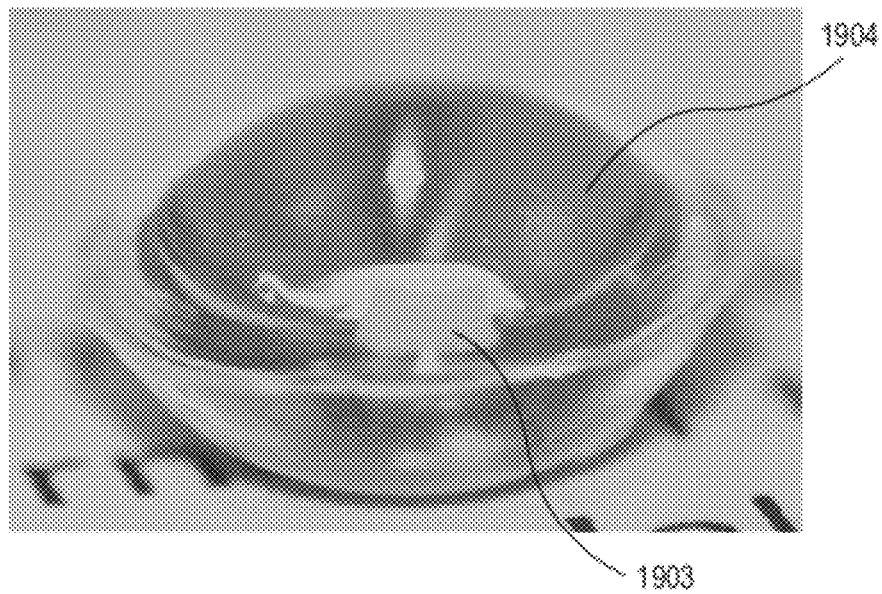
FIG. 19A is a picture of a 30 µm silicon elastomer shell fused on two halves around the equator and entry valve in accordance with an embodiment.
Figure 19B:
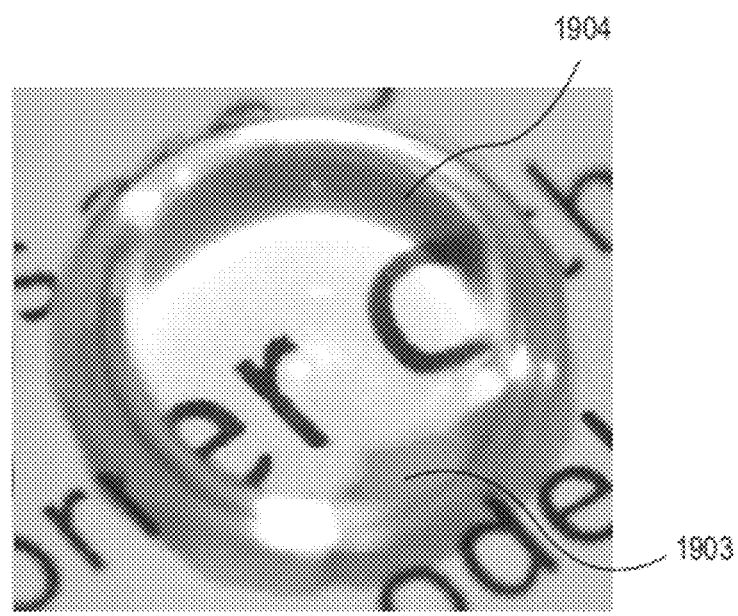
FIG. 19B is an elevated picture of the shell of FIG. 19A.

FIGS. 19A-19B are pictures of a 30 μm silicon elastomer shell fused on two halves around the equator and entry valve in accordance with an embodiment. A (square) rectangular entry valve patch is colored yellow so that a surgeon can easily locate it. A circular shape can also be used, among other shapes. Patch 1903 has an innermost edge (toward the center of the lens) that is concave, specifically shaped as an arc with a center corresponding to the central axis of the lens. This provides an unobstructed circular clear aperture of the lens.

Figure 20A:
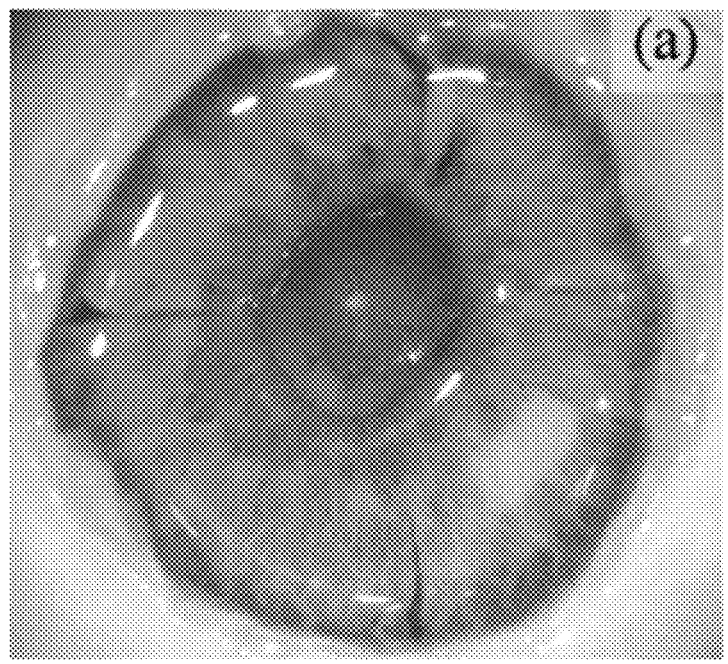
FIG. 20A is a picture of an intraocular lens implanted in a cadaver human eye in accordance with an embodiment.
Figure 20B:
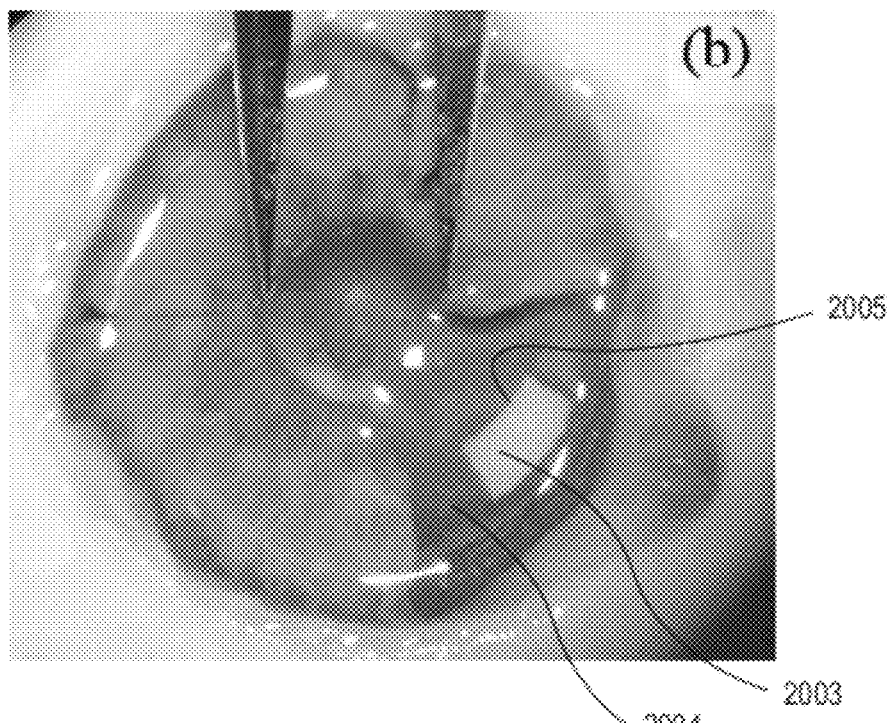
FIG. 20B is a picture of the implanted intraocular lens of FIG. 20A with a section of the iris removed to show a lens patch (valve).

FIGS. 20A-20B are a picture of an intraocular lens implanted in a cadaver human eye in accordance with an embodiment. A rectangular patch valve is visible in the lower right quadrant of the eye in FIG. 20A. In FIG. 20B a section of the eye's iris is removed to show lens patch valve 2003 on intraocular lens 2004. Innermost edge 2005 is arcuate, following a constant radius around the center of the optical axis but set just beyond the optical path of the eye for a fully dilated pupil.

Figure 21A:
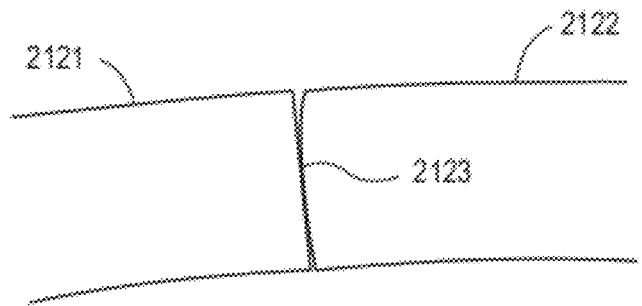
FIG. 21A is a side elevation view of an intraocular lens patch with a slit that is closed in accordance with an embodiment.
Figure 21B:
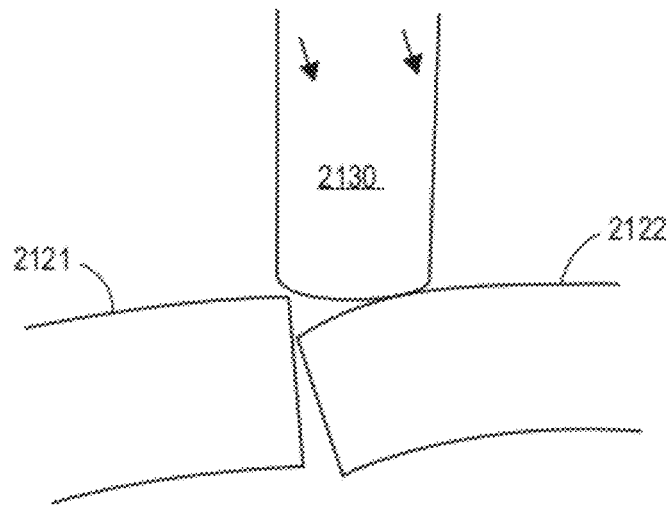
FIG. 21B is a side elevation view of the intraocular lens patch of FIG. 21A that is about to be pierced by a needle.
Figure 21C:
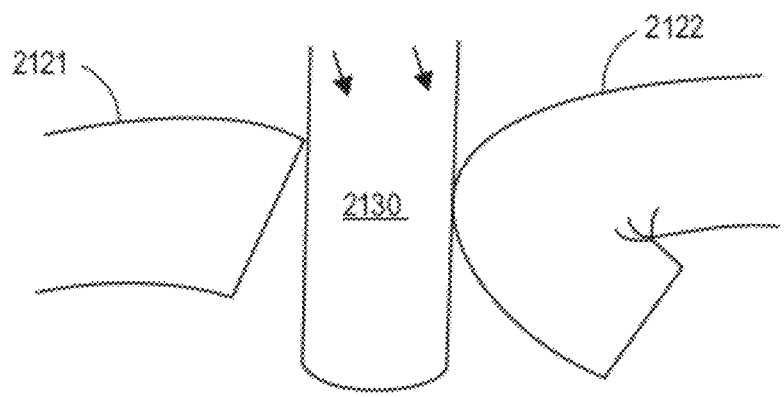
FIG. 21C is a side elevation view of the intraocular lens patch of FIG. 21B that is pierced by a needle.

FIGS. 21A-21C are side elevation views of an intraocular lens patch with a pre-formed slit in accordance with an embodiment. Left side 2121 and right side 2122 of preformed slit 2123 are shown in a closed configuration in FIG. 21A. Fluid from below is sealed in by the patch because elastomeric stresses seal the slit tight. In FIG. 21B, needle 2130 begins to move down and, imperfectly to the left, against the slit to gain entry. Slit 2123 begins to open. In FIG. 21C, needle 2130 juts through the slit, bending left side 2121 and slightly crumpling elastomeric right side 2122. Sides 2121 and 2122 seal against the outside diameter of needle 2130, keeping fluid from inside the lens from leaking out.

Figure 22A:
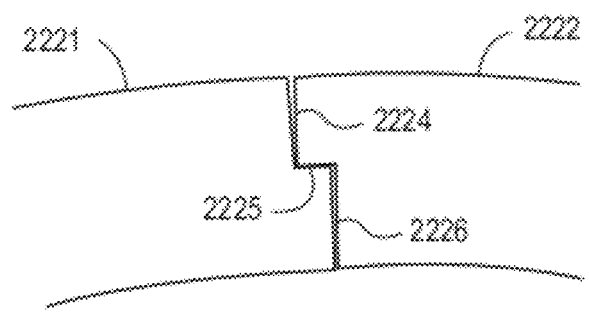
FIG. 22A is a side elevation view of an intraocular lens patch with a stepped slit that is closed in accordance with an embodiment.
Figure 22B:
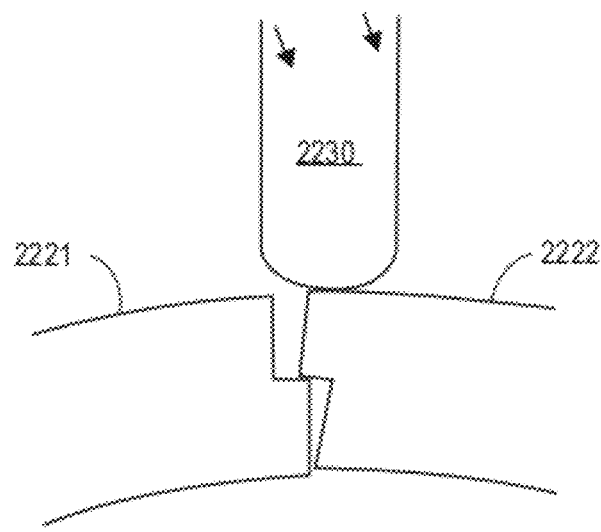
FIG. 22B is a side elevation view of the intraocular lens patch of FIG. 22A that is about to be pierced by a needle.
Figure 22C:
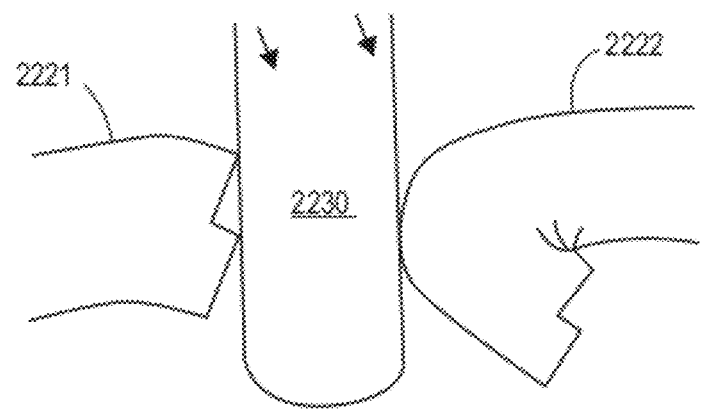
FIG. 22C is a side elevation view of the intraocular lens patch of FIG. 22B that is pierced by a needle.

FIGS. 22A-22C are side elevation views of an intraocular lens patch with a stepped slit in accordance with an embodiment. Left side 2221 and right side 2222 of preformed slit 2224 are closed due to elastomeric stresses in FIG. 22A. Slit 2224 has shelf or stepped portion 2225, which joins slit 2224 with lower portion of slit 2226. The shelf is similar to using a needle to make an incision at an angle. In FIG. 22B, needle 2230 begins to move down and, imperfectly to the left, against the slit to gain entry to the lens. In FIG. 22C, needle 2230 just through the slit, bending left side 2221 and slightly crumpling elastomeric right side 2222. Sides 2221 and 2222 seal against the outside diameter of needle 2230, keeping fluid from inside the lens from leaking out.

It has been found that elastomeric patches of 100 μm or greater are thick enough to self-close for many standard needles. A patch of 160 μm and thicker work with 362 μm diameter standard 28-gauge needles. A patch of 250 μm gives a factor of safety for the 28-gauge needle. This works for nominal pressures within the lens of under 1 psi, which change by 0.06 psi during accommodation.

A needle for injecting or removing fluid from the intraocular lens can be 908 μm diameter (20-gauge), 362 μm diameter (28-gauge), 311 μm diameter (30-gauge), 110 μm diameter (36-gauge), or other sizes. The smaller the needle to be used, the thinner the patch (as shown in FIG. 10).

A plurality of patches can be used to allow for multiple ports in the lens. One port can be used for filling or removing optically clear fluid from the lens, while another port can simultaneously remove air bubbles from an out-pocket.

The invention has been described with reference to various specific and illustrative embodiments. However, it should be understood that many variations and modifications may be made while remaining within the spirit and scope of the following claims.

What is claimed is:

1. An accommodating intraocular lens apparatus, comprising:
   a biocompatible polymer balloon of a first elastomeric material, the balloon fillable with an optically clear medium, the balloon configured for insertion into a capsular bag of an eye; and a valve including a self-sealing elastomeric patch of a different, second, cured elastomeric material that is stiffer than the first material, the elastomeric patch intimately formed with the balloon and being stiffer than the balloon, wherein the balloon has a thickness less than 100 μm, wherein the elastomeric patch has a thickness equal to or between 100 μm and 700 μm, thereby being thin enough to avoid contact with a posterior iris when implanted in an eye and sufficiently thick enough for self-sealing of needle punctures at nominal lens pressures for filling or adjusting said optically clear medium within the balloon, wherein the elastomeric patch includes a pre-formed slit.

2. The apparatus of claim 1 wherein the elastomeric patch has a thickness between 160 μm and 350 μm.

3. The apparatus of claim 1 wherein the elastomeric patch has a thickness between 150 μm and 250 μm.

4. The apparatus of claim 1 wherein the elastomeric patch is colored differently from the balloon, thereby allowing a surgeon to locate the patch.

5. The apparatus of claim 1 wherein the pre-formed slit is adapted for a blunt needle to pass therethrough.

6. The apparatus of claim 5 wherein the pre-formed slit includes a stepped portion.

7. The apparatus of claim 1 wherein the elastomeric patch has a concave innermost edge, the concave edge of the patch located outside an optical path of the lens apparatus.

8. The apparatus of claim 1 further including:
a circumferential sharp edge on an anterior side of the balloon configured to prevent migration of cells across the edge.

9. The apparatus of claim 1 further including:
a circumferential sharp edge on a posterior side of the balloon configured to prevent migration of cells across the edge.

10. The apparatus of claim 1 wherein the balloon comprises a composite of silicone and fluorosilicone.

11. The apparatus of claim 1 wherein the balloon comprises a composite of silicone and parylene.

12. The apparatus of claim 1 wherein the balloon is comprised of parylene and the patch is comprised of a silicone elastomer.

13. The apparatus of claim 1 further comprising an optically clear medium, the optically clear medium attenuating blue or shorter-wavelength electromagnetic radiation.

14. The apparatus of claim 1 wherein the balloon is substantially empty and in a rolled configuration.

15. The apparatus of claim 1 wherein the balloon has a thickness of 30 μm to 40 μm.

16. The apparatus of claim 1 wherein the first and second elastomeric materials comprise silicones.

17. The apparatus of claim 16 wherein the first and second elastomeric materials comprise differently cured silicones.

* * * * *